(12) United States Patent
Carson et al.

(10) Patent No.: US 7,226,457 B2
(45) Date of Patent: Jun. 5, 2007

(54) EPIDERMAL SAMPLING APPARATUS AND METHOD

(75) Inventors: Robert Carson, Rahway, NJ (US); Susanne Teklits Iobst, Maywood, NJ (US); Salvatore E. San Philip, Belleville, NJ (US); Christina H. Arce, Cliffside Park, NJ (US); Carol Feinberg, Wayne, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 693 days.

(21) Appl. No.: 10/370,390

(22) Filed: Feb. 19, 2003

(65) Prior Publication Data

US 2004/0162566 A1    Aug. 19, 2004

(51) Int. Cl.
*A61B 17/50* (2006.01)
*A61B 10/02* (2006.01)

(52) U.S. Cl. .................. 606/131; 600/562; 600/564

(58) Field of Classification Search ............... 606/131, 606/161, 172, 180; 600/562, 564, 567, 570; 433/1; 604/289; 279/51, 57
See application file for complete search history.

(56) References Cited

U.S. PATENT DOCUMENTS

| | | | |
|---|---|---|---|
| 2,658,538 A * | 11/1953 | Kitterman | 81/57.42 |
| 2,712,823 A | 7/1955 | Kurtin | |
| 2,867,214 A | 1/1959 | Wilson | |
| 3,468,079 A | 9/1969 | Kaufman | |
| 4,274,419 A | 6/1981 | Tam et al. | |
| 4,538,612 A | 9/1985 | Patrick, Jr. | |
| 5,325,857 A | 7/1994 | Nabai et al. | |
| 5,380,337 A | 1/1995 | Romaine | |
| 5,394,886 A | 3/1995 | Nabai et al. | |
| 5,570,700 A | 11/1996 | Vogeler | |
| 5,707,383 A | 1/1998 | Bays et al. | |
| 5,800,446 A | 9/1998 | Banuchi | |
| 5,879,326 A | 3/1999 | Godshall et al. | |
| 6,136,008 A | 10/2000 | Becker et al. | |
| 6,241,739 B1 | 6/2001 | Waldron | |
| 6,258,044 B1 | 7/2001 | Lonky et al. | |
| 6,283,978 B1 | 9/2001 | Cheski et al. | |
| 6,299,620 B1 | 10/2001 | Shadduck et al. | |
| 6,387,103 B2 | 5/2002 | Shadduck | |
| 6,423,078 B1 | 7/2002 | Bays et al. | |
| 2001/0018061 A1 | 8/2001 | Rhoades | |
| 2002/0045907 A1 | 4/2002 | Sherman et al. | |
| 2002/0087167 A1 | 7/2002 | Winitsky | |
| 2002/0087168 A1 | 7/2002 | Winitsky | |
| 2002/0107527 A1 | 8/2002 | Burres | |
| 2002/0123675 A1 | 9/2002 | Trautman et al. | |
| 2002/0143345 A1 | 10/2002 | Koefer et al. | |
| 2004/0162565 A1* | 8/2004 | Carson et al. | 606/131 |

FOREIGN PATENT DOCUMENTS

| | | |
|---|---|---|
| EP | 1 086 719 A1 | 3/2001 |
| EP | 1 219 254 | 3/2002 |
| FR | 2791433 | 9/2000 |
| GB | 2278282 | * 11/1994 |
| RU | 2184491 | 7/2002 |
| WO | 03096905 | 11/2003 |

* cited by examiner

OTHER PUBLICATIONS

International Search Report, PCT/EP2004/000657, dated May 27, 2004.

*Primary Examiner*—Anhtuan T. Nguyen
*Assistant Examiner*—Tuan V. Nguyen

(57) ABSTRACT

Apparatus for abrading a small sample of epidermis for bio-analytical processing and method of using same. The apparatus removes small samples of epidermal tissue with efficiency, minimal discomfort, and no excess tissue removal. The apparatus and method may be provided as part of a home-use kit for individualized analysis.

12 Claims, 3 Drawing Sheets

EPIDERMAL SAMPLING APPARATUS AND METHOD

FIELD OF THE INVENTION

The present invention relates to an epidermal sampling apparatus and method. More particularly, the present invention relates to an epidermal sampling device and method for painlessly and bloodlessly sampling skin for analysis.

BACKGROUND OF THE INVENTION

Demonstrating efficacy of technology on human subjects is an essential part of successful achievement of commercialization of such technology. Human trials aimed at identifying benefits of a technology, such as a skin benefit technology, often require three to six months duration to visualize measurable effect. For example, retinoids are a particularly potent anti-aging technology in skin care, however, even retinoids require this lengthy period to elicit a visual change. Shorter term, e.g. 1 week, human studies may be developed. These shorter term studies are especially useful for screening or ranking a number of potential actives. Short term human studies rely on the collection of skin tissue samples which are typically undertaken by physicians taking relatively invasive biopsies of the skin, either full thickness (dermis and epidermis) or shave biopsies. These invasive skin sampling methods generally provide more tissue than is actually required for many assays for biomarkers which may indicate long term clinical efficacy after short term treatment.

Currently used sampling techniques include the following: full thickness punch biopsies, "nick" (small shave) biopsies and blister biopsies. Full thickness punch biopsies entail use of a razor-edged circular punch and a scalpel to remove a piece of tissue that can extend further than the dermis. "Nick" or small shave biopsies involve the use of a scalpel to remove a pinched up portion of the skin surface and the third requires the use of a vacuum applied to the skin surface to produce a blister, which is removed by scalpel. The full thickness punch biopsy and the small shave biopsy techniques present the subject with considerable discomfort, require anesthesia (administered by a physician), and pose potential harm. Methods of this type, involving gross removal of skin tissue in a procedure that is essentially surgical include: U.S. Pat. Nos. 5,325,857, 5,394,886, 5,380,337 and 5,570,700. Blister biopsies require the use of a vacuum applied to the skin surface to produce a blister, which is removed by scalpel. Suction blister epidermal sampling provides the desired epidermal samples, however, this method requires a blistering period of about two hours, during which time changes can occur to the biochemistry of the epidermal skin cells, such as the degradation of RNA.

Dermabrasion tools and techniques used in treating pitted and disfigured skin involve what are essentially power tools and involve no harvesting and processing of sampled tissue material. U.S. Pat. No. 6,423,078 relates to surgical abrasion using diamond grit and U.S. Pat. No. 5,800,446 relates to an abrasive tip, however, both of these devices remove considerably more tissue than they are able to harvest.

There is a need for a sampling apparatus and technique that does not require the presence of a physician, is minimally invasive, does not remove excess tissue, can be done with minimal discomfort and that provides a sample large enough for biochemical analysis.

SUMMARY OF THE INVENTION

To attenuate the shortcomings of the prior devices and techniques, a novel epidermal sampling device, apparatus, and technique have been developed.

In a first aspect, the present invention provides an abrasion device assembly for sampling small amounts of epidermal cells from a skin surface of an individual. The assembly includes an abrasion device powered by a motor. The abrasion device includes an actuator device comprising a cylindrical central shaft having a proximal end and a distal end and including a spring at the proximal end. The central shaft has a handle integral therewith which protrudes therefrom at a selected position between the proximal end and the distal end. The central shaft has a central opening situated therein, extending from the proximal end to the distal end thereof. A collet is provided at the proximal end within the central shaft. Also provided within the central shaft is a cylindrical threaded rod extending from a connection with the collet toward the distal end.

A probe may be disposed centrally and releasably within the central opening of the actuator device, and more specifically, the probe is releasably held by the collet. The probe comprises a cylindrical rod having a distal end and terminating in an abrasive surface at a cross-sectional proximal end thereof. The abrasive surface is appropriately textured and has a small cross-sectional diameter for abrasion and harvesting of epidermal cells. The abrasive surface includes a flat surface area having a plurality of peaks and troughs extending therefrom and positioned along the flat surface area in any random configuration. The configuration of peaks and troughs may include a patterned configuration. Preferably, the peaks have a cross-sectional geometric shape that includes an angle, selected from the group consisting of a triangle, rectangle, hemisphere, trapezoid, or a combination thereof. Most preferably, the troughs have a cross-sectional geometry of a hemisphere. The number and size of peaks and troughs are determined by the criteria that the Harvesting Volume be greater than or equal to the Abrasion Volume.

A positioning sleeve positioned over the actuator device is provided, so that a desired length of the probe extends therefrom. The positioning sleeve comprises a frustaconical portion of a larger diameter than the central shaft. The positioning sleeve has a proximal end and a distal end and a cylindrical cap portion removably positioned at the proximal end.

In another aspect, the invention provides a method for sampling small amounts of epidermal cells from a skin surface of an individual, comprising providing an abrasion device assembly according to the first aspect. Upon being pressed against the skin surface with the abrasive surface, the probe abrades a small sample of epidermal tissue. After the sample is taken, the probe is released from the housing and the sample on the abrasive surface is submitted for analysis. The amount sampled is about 0.00001 cubic cm to about 0.001 cubic cm. Bio-analytical analysis may be performed, such as analysis of RNA, protein, genomic DNA, minerals and other metabolites, and combinations thereof.

In a further aspect, the present invention provides a kit including the abrasion assembly. The kit may be suitable for consumer use and not require a physician's assistance.

For a more complete understanding of the above and other features and advantages of the invention, reference should be made to the following description of the preferred embodiment.

BRIEF DESCRIPTION OF THE DRAWINGS

The invention will be better understood by way of the following detailed description of a preferred embodiment, with reference to the appended drawings in which.

DETAILED DESCRIPTION OF THE INVENTION

As used herein, the term "comprising" means including, made up of, composed of, consisting and/or consisting essentially of. Except in the operating and comparative examples, or where otherwise explicitly indicated, all numbers in this description indicating amounts or ratios of material or conditions of reaction, physical properties of materials and/or use are to be understood as modified by the word "about".

The term "harvesting" as used herein refers to the picking up of debris of abraded epidermal cells.

The term "skin" as used herein includes the skin on or in the face, mouth (epithelial cells), neck, chest, back, arms, hands, legs, and scalp.

The apparatus and method of the present invention involve the removal of the upper skin layer with a manual/semi-automatic, mechanically driven, abrasive probe. Using the inventive apparatus and method, the epidermis, including the basal layer of the epidermis, is removed, thereby effectively sampling the whole epidermis. Various quantities of epidermis may be obtained by varying the diameter of the probe. The small quantities of epidermis obtained using the inventive apparatus and method have been found to have great utility in a variety of bio-analytical applications, such as determination of RNA, protein, genomic DNA, minerals and other metabolites.

Figure 1:
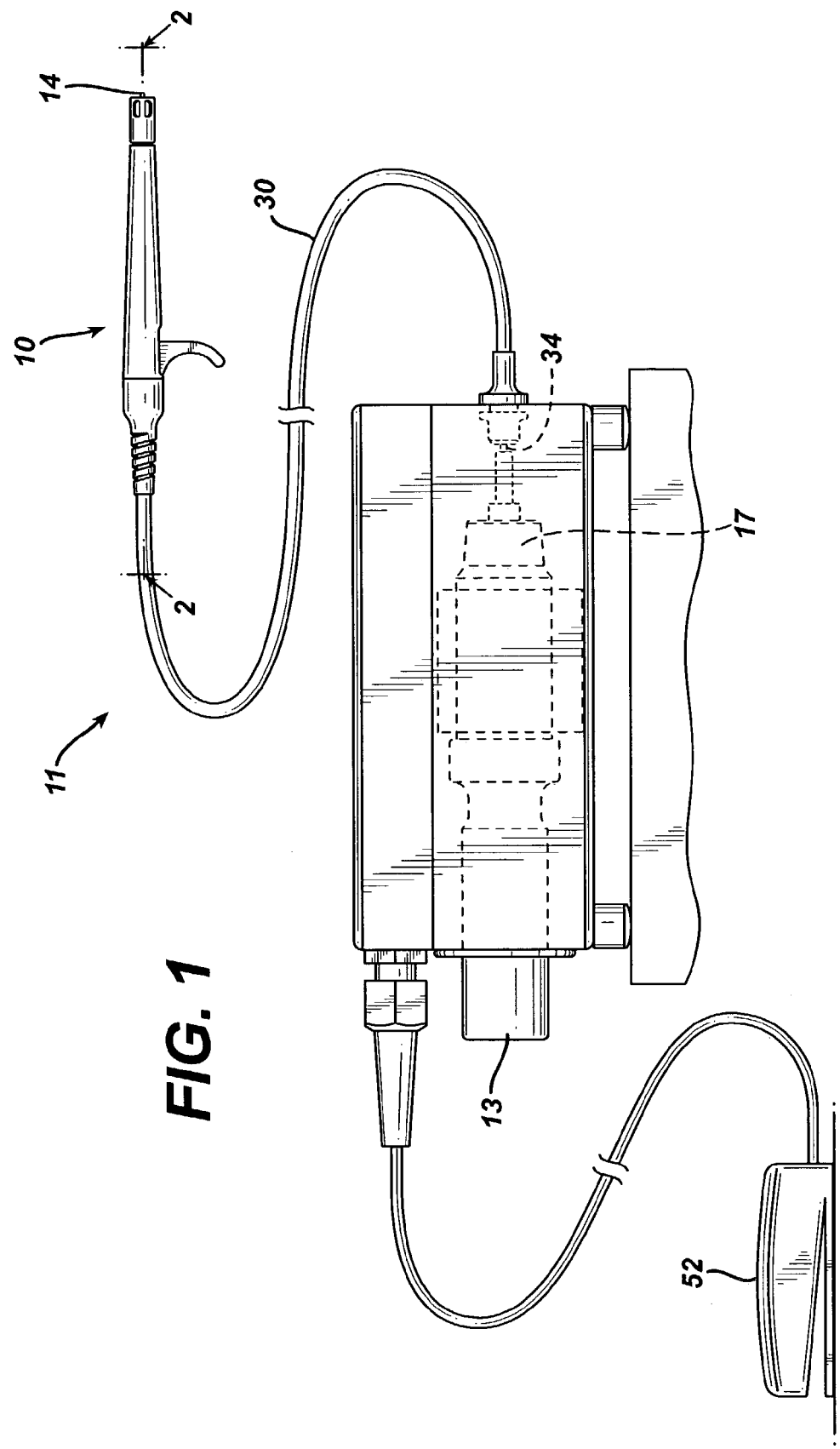
FIG. 1 is a front elevational view of an epidermal sampling apparatus according to a preferred embodiment.

With reference to FIG. 1, an apparatus, referred to herein as abrasion device assembly 11, for sampling small amounts of epidermal cells from a skin surface of an individual includes an abrasion device 10 connected to a semi-automatic actuator drive 13 by a rotatable cable 30. Actuator drive 13 includes screw driver 17 and can be activated by a manual switch 52 which includes a cable portion connected to actuator drive 13.

Figure 2:
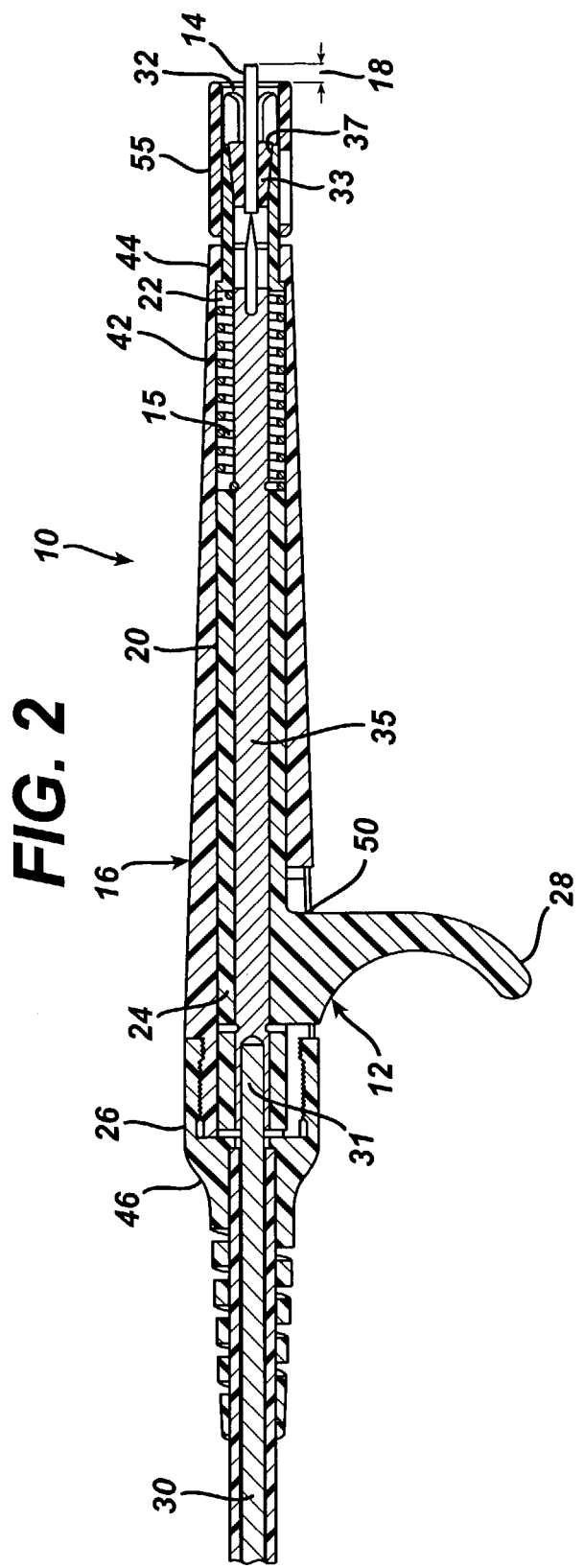
FIG. 2 is a cross-sectional view taken along line 2—2 in FIG. 1.

With reference to FIG. 2, abrasion device 10 includes an actuator device 12, probe 14, appropriately sized to cooperate with and be centrally and releasably seatable within actuator device 12, and a sleeve 16 positioned over actuator device 12.

Actuator device 12 includes a cylindrical central shaft 20 having a proximal end 22 and a distal end 24 having a spring 15 extending from a position adjacent proximal end 22 of shaft 20 in the direction of probe 14. Central shaft 20 includes a handle 28 integral therewith and protruding therefrom at a selected position 50 between proximal end 22 and distal end 24, preferably closer to distal end 24. Central shaft 20 has a central opening 32 situated therein, cylindrical for the most part and frusta-conical in shape past spring 15 toward proximal end 22, forming a seat 37 for holding a collet 33 which is capable of receiving and holding probe 14. Collet 33 is connected to a driver rod 35 also disposed within central opening 32 whereby the driver rod 35 may be threaded at its proximal end to facilitate the connection of collet 33 to the same.

Sleeve 16 includes a frusta-conical portion 42 of a larger diameter than central shaft 20 having a proximal end 44 and a distal end 46 and a cylindrical cap portion 55 having one or more cavities therein removably positioned at proximal end 44 and allowing a desired length 18 of probe 14 to extend therefrom. Sleeve 16 further terminates in cap 26 at distal end 46 thereof.

With reference to FIGS. 1 and 2, abrasion device 10 is further equipped with a rotatable cable 30, one end 31 of which may be seated within sleeve 16 of abrasion device 10, at distal end 46, by insertion into opening 32 and cooperation with driver rod 35, while the other end 34 of which may be connected to a screw driver 17 which in turn is connected to and powered by an automatic motor 13 equipped with a switch 52.

Figure 3:
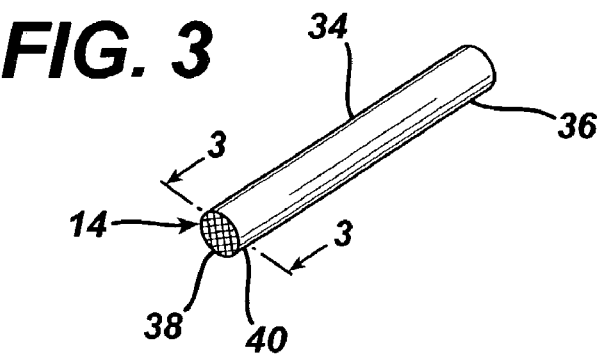
FIG. 3 is a perspective view of the probe of the epidermal sampling apparatus of FIG. 2.
Figure 4:
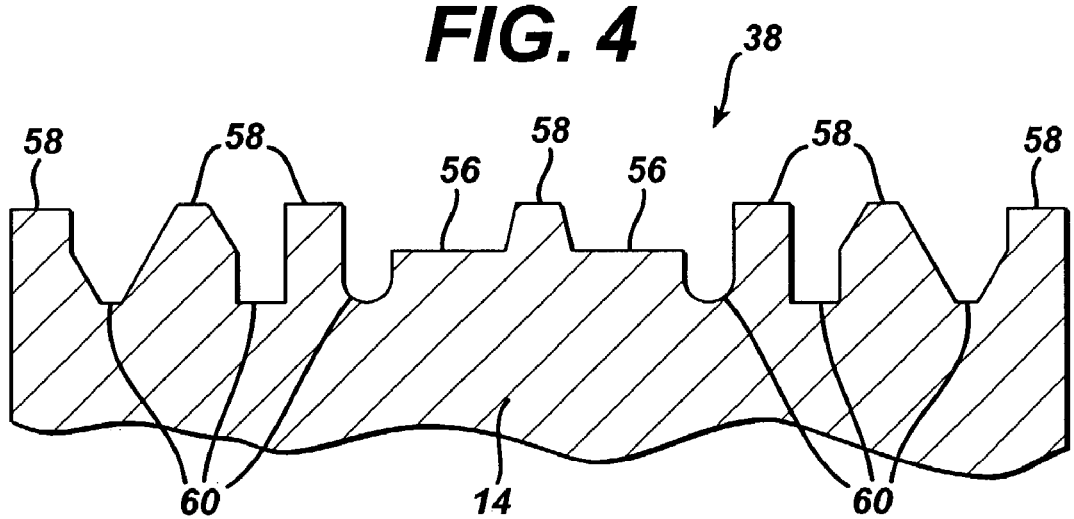
FIG. 4 is a cross-sectional view taken along line 3—3 in FIG. 3.
Figure 5:
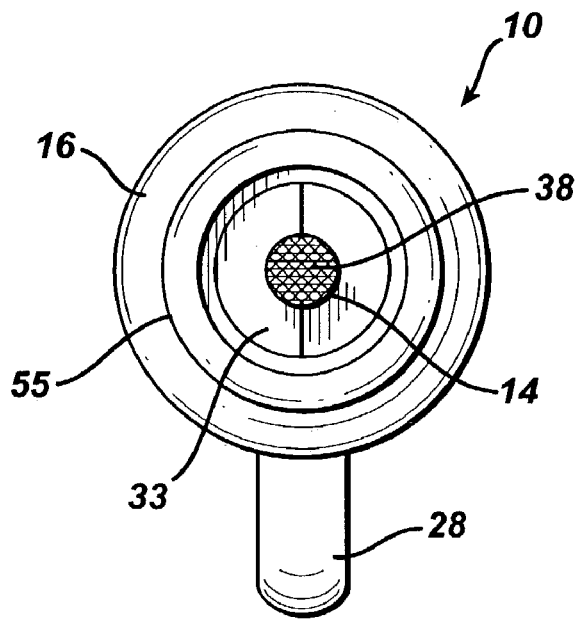
FIG. 5 is an enlarged top view of the abrasive surface of a probe in the epidermal sampling apparatus of FIG. 1.

With reference to FIG. 3, probe 14 includes a cylindrical rod 34 having a distal end 36 and terminating in an abrasive surface 38 at a cross-sectional proximal end 40 thereof, which may be in the form of a disk, and appropriately textured for abrasion. To be appropriate, the texture of abrasive surface 38 will not work it if is too fine; on the other hand, it will not work if it is too rough, as will be further discussed hereinbelow. Rod 34 may be of any small size suitable for sampling epidermal tissue and appropriately sized to cooperate with collet 33. Preferably, rod 34 is about 1 mm to about 10 mm in cross-sectional diameter. Cylindrical rod 34, and in turn abrasive surface 38, preferably has a diameter of about 1.5 mm.

With reference to FIG. 3, abrasive surface 38 of probe 14 includes a flat surface area 56 having a plurality of peaks 58 and troughs 60 extending upward and downward, respectively, relative thereto and positioned along flat surface area 56 in any configuration, including random or patterned configuration. Preferably, the configuration of peaks 58 and troughs 60 will be patterned, or symmetrical, due to ease of manufacture.

Peaks 58 and troughs 60 may be of any three-dimensional shape, thereby having any cross-sectional shape. Preferably, for better abrasion, the cross-sectional shape of peaks 58 (or troughs 60 in the absence of peaks 58) includes an angle relative to the plane of flat surface area 56, such as that of a triangle, rectangle, hemisphere, trapezoid, or another geometry including an angle. More preferably, the cross-sectional geometrical shape includes a sharp angle that will form a sharp edge in the overall three-dimensional shape of peaks 58 or troughs 60.

Most preferably, the cross-sectional geometry of troughs 60 is a hemisphere for maximum capacity.

In one aspect of the invention, abrasive surface 38 may be comprised of only troughs 60. In another aspect, abrasive surface 38 may be comprised of only peaks 58.

The number and size of peaks 58 and troughs 60 is determined by the criteria that the Harvesting Volume be greater than or equal to the Abrasion Volume. Harvesting Volume as referred to herein is intended to mean the volume capacity of the sum of the volumes of troughs 60 plus the interstitial volume between peaks 58 (if any), while Abrasion Volume as referred to herein is intended to mean the volume of skin sample collected. This criteria ensures that substantially all the tissue abraded shall be harvested.

Preferably, probe 14 rotation is achieved automatically and allows for storage and quick access to multiple probes for multiple sampling.

With reference to FIGS. 1 and 2, to assemble, probe 14 is inserted into collet 33 in central opening 32 of central shaft 20 of abrasion device 10. Cap 55 of sleeve 16 is slid over central shaft 20, allowing desired length 18 of probe 14 to protrude and extend beyond proximal end 44 of positioning sleeve 16. Desired length 18 is determined by the degree of pressure desired to be applied against the skin in such a way as to avoid excessive penetration of the skin layers below the epidermis. Preferably, the depth of skin penetration is about 100 micro m.

To dis-assemble, probe 14 is released from abrasion device 10 by depressing handle 28 in the direction of proximal end 22 of central shaft 20, thereby applying pressure to collet 33 by way of movement of shaft 20 which applies pressure to spring 15, in turn applying pressure to and causing collet 33 to be released from seat 37 and partially exit central opening 32, allowing it to expand and release probe 14. Subsequently, when handle 28 is released, collet 33 springs back in seat 37.

In use, after sterilizing probe 14 or a plurality of probes 14 and assembling abrasion device 10, motor 13 is activated with a manual switch 52, causing screw driver 17 to rotate and in turn causing cable 30 to rotate, thereby causing driver rod 35 to rotate which, in turn, causes rotation of probe 14, wherein upon being pressed lightly against the skin surface with abrasive surface 38, probe 14 abrades a small sample of epidermal tissue by the rotating action against the skin.

Desired length 18 of protrusion of probe 14 is adjusted by the length of cap 55, thereby allowing for control of pressure applied to the skin and preventing excessive penetration of the skin, as well as preventing contact with nerves and avoiding the sensation of pain. Flat surface area 56 of abrasive surface 38 of probe 14 also provides control of the depth of abrasion, as the probe will tend not to penetrate beyond the contact of skin with flat surface area 56. Rotation effectively removes epidermal tissue, which adheres to abrasive surface 38. Small amounts of epidermal tissue are removed, preferably about 0.00001 cu cm to about 0.001 cu cm, more preferably about 0.0003 cu cm (about 300 micro g). After the sample is taken, probe 14 is released from central opening 32 (as described hereinabove with reference to dis-assembly), and the epidermal sample collected on or in abrasive surface 38 may be submitted for analysis. Suitable analyses include biochemical markers, RNA, protein, genomic DNA, minerals and other metabolites.

The abrasion device 10 allows quick, substantially bloodless epidermal sample excission (unlike biopsies), and leaves minimal or no residual scar (unlike surgical biopsies). Compared to the suction blistering technique which takes about two hours and punch biopsy, which takes about two minutes, abrasion may be performed in about 0.001 to 60 seconds, preferably about 3 seconds. The speed of sampling offers the advantage of obtaining real time samples and limits sample degradation.

The inventive device and method advantageously provide efficiency, minimal discomfort, avoidance of excess tissue removal and scarring, and the capability to efficiently harvest and collect epidermal samples for analysis. The small amount of epidermis which is sampled results in minimal discomfort to the subject and a substantial absence of scar. The device therefore lends itself to multiple sampling from one individual. Therefore, the device and method are useful in investigations of individual variation in skin biology and product efficacy, such as for example providing crucial tissue sampling to enable genomic analysis of skin to be assessed before and after product application. The device and method may also be useful in skin diagnostic activities.

This technique could be widely employed in clinical testing as it is minimally invasive and much more acceptable to subjects than current sampling methods. It also may be capable of adaptation for home-use skin sampling/analysis kits, which may include abrasion device assembly 11 together with instructions for use and analysis and an analytical device.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the inventions be limited only by the scope of the claims which follow, and that such claims be interpreted as broadly as is reasonable. Throughout this application, various publications have been cited. The entireties of each of these publications are hereby incorporated by reference herein.

The invention claimed is:

1. An abrasion device assembly for sampling small amounts of epidermal cells from a skin surface of an individual includes an abrasion device connected to a motor; said abrasion device comprising:
    an actuator device comprising a cylindrical central shaft having a proximal end and a distal end and including a spring at said proximal end; said central shaft comprising a handle integral therewith and protruding therefrom at a selected position between said proximal end and said distal end; said central shaft having a central opening situated therein, extending from said proximal end to said distal end thereof, holding a collet at said proximal end and a driver rod extending from a connection with said collet toward said distal end;
    a probe capable of being disposed centrally and releasably within said central opening of said actuator device; said probe comprising a cylindrical rod having a distal end and terminating in an abrasive surface at a cross-sectional proximal end thereof; said abrasive surface being appropriately textured and having a small cross-sectional diameter for abrasion and harvesting of said epidemial cells; and
    a positioning sleeve positioned over said actuator device so that a desired length of said probe extends therefrom, comprising a frustaconical portion of a larger diameter than said central shaft, having a proximal end and a distal end and a cylindrical cap portion removably positioned at said proximal end.

2. The abrasion assembly of claim 1, wherein said abrasive surface includes a flat surface area having a plurality of peaks and troughs extending therefrom and positioned along said flat surface area in any random configuration.

3. The abrasion assembly of claim 1, wherein said configuration of peaks and troughs includes a patterned configuration.

4. The abrasion assembly of claim 1, wherein said peaks have a cross-sectional geometric shape that includes an angle, selected from the group consisting of a triangle, rectangle, hemisphere, trapezoid, or a combination thereof.

5. The abrasion assembly of claim 1, wherein said troughs have a cross-sectional geometry of a hemisphere.

6. The abrasion assembly of claim 1, wherein the number and size of peaks and troughs is determined by the criteria that the Harvesting Volume be greater than or equal to the Abrasion Volume.

7. A method for sampling small amounts of epidemial cells from a skin surface of an individual, comprising providing an abrasion device assembly according to claim 1; wherein upon being pressed against said skin surface with said abrasive surface said probe is capable of abrading a small sample of said epidermal tissue.

8. The method of claim 7, wherein, after said sample is taken said probe is released from said housing and said sample on said abrasive surface is submitted for analysis.

9. The method of claim 7, wherein said amount sampled is about 0.00001 cubic cm to about 0.001 cubic cm.

10. The method of claim 7, further comprising bio-analytical analysis selected from the group consisting of analysis of RNA, protein, genomic DNA, minerals and other metabolites, and combinations thereof.

11. A kit including the abrasion assembly of claim 1.

12. The kit of claim 11, wherein use of said kit by a consumer does not require the assistance of a physician.

* * * * *